United States Patent
Dietz

(10) Patent No.: US 11,717,223 B2
(45) Date of Patent: Aug. 8, 2023

(54) METHODS, SYSTEMS, AND DEVICES FOR DETERMINING AND MAINTAINING A CONSISTENT GROUND AND GROUND SATURATION RESISTANCE

(71) Applicant: PROLUNG, INC., Salt Lake City, UT (US)

(72) Inventor: Phillip W. Dietz, Saint George, UT (US)

(73) Assignee: PROLUNG, INC., Salt Lake City, UT (US)

( * ) Notice: Subject to any disclaimer, the term of this patent is extended or adjusted under 35 U.S.C. 154(b) by 768 days.

(21) Appl. No.: 16/597,667

(22) Filed: Oct. 9, 2019

(65) Prior Publication Data

US 2020/0107784 A1 Apr. 9, 2020

Related U.S. Application Data

(60) Provisional application No. 62/743,432, filed on Oct. 9, 2018.

(51) Int. Cl.
| | |
|---|---|
| *A61B 5/00* | (2006.01) |
| *A61B 5/24* | (2021.01) |
| *A61H 39/00* | (2006.01) |
| *A61B 5/0532* | (2021.01) |
| *A61B 18/16* | (2006.01) |

(52) U.S. Cl.
CPC .......... *A61B 5/6887* (2013.01); *A61B 5/0532* (2013.01); *A61B 5/24* (2021.01); *A61B 5/6814* (2013.01); *A61B 18/16* (2013.01); *A61H 39/002* (2013.01)

(58) Field of Classification Search
None
See application file for complete search history.

(56) References Cited

U.S. PATENT DOCUMENTS

| | | | |
|---|---|---|---|
| 4,445,384 A | 5/1984 | Royer | |
| 5,202,098 A | 4/1993 | Nichols | |
| 6,241,762 B1 | 6/2001 | Shanley | |
| 6,299,586 B1 * | 10/2001 | Cao | A61H 39/002 601/134 |
| 6,746,890 B2 | 6/2004 | Gupta et al. | |
| 7,729,784 B2 | 6/2010 | Mills et al. | |
| 8,548,556 B2 * | 10/2013 | Jensen | A61B 5/0537 600/384 |
| 9,339,641 B2 | 5/2016 | Rajguru et al. | |
| 2004/0054275 A1 | 3/2004 | Finneran et al. | |
| 2009/0120801 A1 | 5/2009 | Zhou | |
| 2009/0314616 A1 | 12/2009 | Oberhammer | |

* cited by examiner

*Primary Examiner* — Douglas X Rodriguez
(74) *Attorney, Agent, or Firm* — Kunzler Bean & Adamson

(57) ABSTRACT

The disclosure extends to systems and devices for determining and maintaining a consistent ground and ground saturation resistance that include a device that includes a grip element and bioelectrical grounding segments, which may be disposed about the grip element on the grounding device.

20 Claims, 5 Drawing Sheets

METHODS, SYSTEMS, AND DEVICES FOR DETERMINING AND MAINTAINING A CONSISTENT GROUND AND GROUND SATURATION RESISTANCE

PRIORITY CLAIM

This application claims the benefit of U.S. Provisional Application No. 62/743,432, filed Oct. 9, 2018, which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure relates to methods, systems, and devices for determining and maintaining a consistent ground and ground saturation resistance, and more particularly to methods, systems, and devices for determining and maintaining a consistent ground and ground saturation resistance in bioelectrical measurements and bio-conductivity testing.

SUMMARY

Described herein is a bioelectrical grounding device that includes a grip element and one or more grounding segment. Further described, is a system that includes a processor that receives from one or more grounding segment a grounding reading. The processor then determines which one or more of the grounding segments are required to reach a ground saturation. The system further includes a grounding device with a grip element and one or more grounding segment.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

Figure 1A:
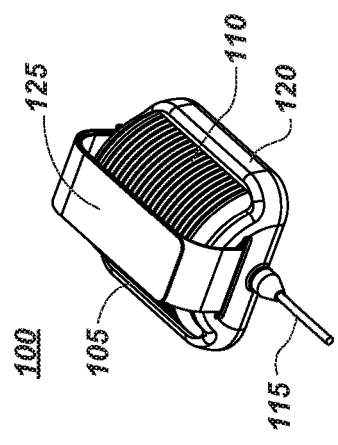
FIGS. 1A-1C illustrate a perspective view, top view, and side view respectively of an arched grounding device with narrowly sized bioelectrical grounding segments.

In the following description, for purposes of explanation and not limitation, specific techniques and embodiments are set forth, such as particular techniques and configurations, in order to provide a thorough understanding of the system and device disclosed herein. While the techniques and embodiments will primarily be described in context with the accompanying drawings, those skilled in the art will further appreciate that the techniques and embodiments may also be practiced in other similar devices.

The disclosure relates to obtaining an electrical conductance reading, sometimes referred to as a bio-conductivity test, from a patient. The methods, systems and devices disclosed may relate to a sensor head for contacting a patient's skin and may also relate to a conductive tip positioned on the sensor head to contact a portion of the patient's skin when the sensor head is placed against the patient's skin to obtain independent measurements of electrical conductance.

The disclosure extends to methods, systems, devices, and computer program products for determining and maintaining a consistent ground and ground saturation resistance, and more particularly to methods, systems, devices, and computer program products for determining and maintaining a consistent ground and ground saturation resistance in bioelectrical measurements and bio-conductivity testing.

In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

Electro Acupuncture according to Vohl (EAV) devices measure the conductance levels at meridian points throughout the human body. An EAV device in its simplest form is a very sensitive ohm meter. Ohm meters are traditionally used to measure resistance, which is measured in Ohms. By understanding and knowing the resistance of a material, tissue, or meridian pathway (in the case of bio-conductivity testing), you can determine the conductivity. The lower the resistance or ohm reading the higher the conductivity.

An Ohm meter has a small DC current flow through a material and the Ohm meter measures the resistance of the material. Resistance measures the relative difficulty to push a current through a material. Electrical conductors are very easy to push current through so they have a low resistance. Electrical insulators are difficult to push a current through so they have a high resistance.

Ohm's Law applies to materials with a proportional relationship between voltage and current: $V=R\,I$ where V is voltage, I is current and R is resistance. Therefore, resistance is measured by: $R=V/I$.

Conductivity is the reciprocal of resistivity. It is the degree to which a specified material conducts electricity, calculated as the ratio of the current density in the material to the electric field that causes the flow of current.

It will be appreciated and understood that human tissue generally has a resistance of 100,000 Ohms. Meridian points have a general resistance of 5,000 Ohms. This means that meridian points throughout the human body are about 20 times as conductive as the tissue surrounding these meridian points. This large differential in conductivity makes it possible to locate meridian points and to be very consistent in verifying the points.

Traditional EAV testing or measuring of meridian points is done by gripping a brass rod (hand mass, or grounding element) in one hand while point readings are taken on the other hand and the other side of the body. Then the brass rod is placed in the other hand while the meridian points on the other side of the body are read. The meridian point readings require a brass tip to make contact with the meridian point and the readings are taken and recorded while pressure is applied to the brass tip against the tissue at that point. Those skilled in the art will recognize that brass is the desirable material used for EAV contacts, however, other conductive materials may be used such as stainless steel.

These meridian points are located under the human skin, which adds to the difficulty in measuring resistance because skin can become dry and act as an insulator. To minimize this insulator effect, it is a standard practice to spray a mist of water on the hand that grips the hand mass to help increase the conductivity of the tissue that is gripping the hand mass or brass rod. The hand mass acts as a ground or a reference.

Another method to decrease this insulator effect is to increase the pressure of the tip against the tissue over the meridian point. Another method is to add moisture or water to the tissue where the reading is taking place. Another method is to have a texture applied to the tip surface that helps penetrate the insulation layer or cornified layer of the tissue without puncturing.

Some in the practice of bio-conductivity testing use small electrodes similar to those used with EKG machines in the place of the brass rod or hand mass. Some also make different sized hand masses to fit different sized hands whether they be a small children or large adults. To be more efficient and effective, this grounding or reference surface needs to be large enough to adequately provide ample ground to take consistent and accurate readings.

As part of the problem the disclosure addresses, it should be noted that when an adult human subject tested uses a large hand mass as compared to a smaller hand mass design often used for smaller subjects, such as children, the readings were lower with the smaller hand mass than they were with the larger hand mass. When the subject switched back to the larger hand mass the readings went back up, which led to issues relating to accuracy of the readings and whether they could be consistent. This led to a test where the adult human subject was given a large hand mass with covered strips of nonconductive tape wrapped around the diameter or perimeter of the brass rod, such that each strip of tape would cover up 5% of the brass rod or hand mass. With 20 strips of tape on the rod the hand mass was completely covered leaving the entire rod nonconductive, the system was unable to take a reading as it was unable to complete a circuit.

When 1 strip of tape was removed, exposing 5% of the conductive brass, a complete electrical circuit was made, resulting in a successful reading. The entire area of the brass rod was about 7 square inches and so each strip of tape basically covered 0.35 square inches. With each removal of a tape strip the reading would increase because the testing circuit had more ground area. As the tape removal continued, the readings incrementally increased with more and more exposure to the grounding area. However, the incremental increase in readings were getting smaller and smaller with each removal of tape until the 11th strip of tape was removed exposing 55% of the conductive area or 3.85 square inches, at which time the readings were stable and no longer changed upon testing at the same point. The readings then remained the same after this point even as more tape was removed until the entire brass was exposed.

More testing revealed that the moisture of the skin could affect the amount of area required to establish ground saturation. The testing revealed that at least 2.8 square inches of ground area was needed with the subject's hand completely dripping wet to establish ground saturation. This minimum required area for ground saturation varies from person to person based, at least in part if not entirely, upon their skin conductivity.

A resistance or Ohm reading required a constant grounding area of a subject's hand that is contacting the hand mass. If the resistance reading of the grounding area remains the same or substantially the same, then the readings become more consistent and repeatable.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein.

Figure 1B:
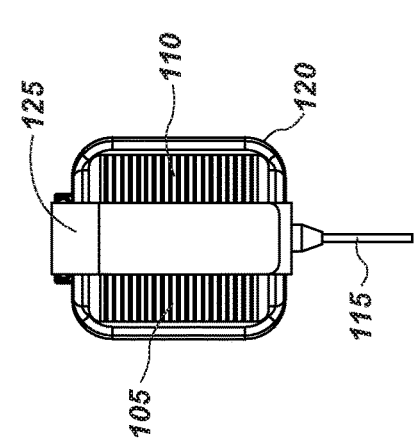
Figure 1C:
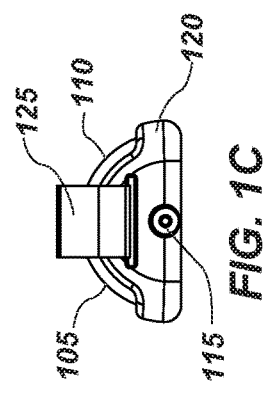

FIGS. 1A-1C illustrate a perspective view, top view, and side view respectively of an arched grounding device with narrowly sized bioelectrical grounding segments 110. Bioelectrical grounding segments 110 may be considered narrow when each segment consists of about 5% of the usable surface area on grip device 105. Narrowly sized bioelectrical grounding segments 110 may range from 1%-9.9% of the usable surface area on a grip device. Intermediately sized surface area of the bioelectrical grounding segments 110 may range from 10%-19.9% of the usable surface area on a grip device. Lastly, widely sized bioelectrical grounding segments 110 would be 20% and greater of the usable surface area on a grip device. The usable surface excludes any side attached to base 120 and any other part not intended to come in contact with a patient's body.

Grounding device 100 is arched to allow the hand to rest comfortably to facilitate contact with grip element 105. Grip element 105 is the part of grounding device that contains grounding segment 110 and is to come in contact with a patient's body usually their hand. Bioelectrical grounding segments 110 can be equal distances apart or they may be place at varying distances along the grip element.

Grip element 105 may have may different shapes and sizes to best meet the needs of the both the user and the patient. For example, grip element 105 may be arched to allow a patient to rest his or her arm on the table while the natural curvature of the hand rest over top of the arched grip element 105. Moreover, grip element 105 may be a flat, hemispherical, cylindrical, double arched etc. and is attached to base 120. To aid in maintaining contact to grip element 105, strap 125 may be placed over the hand, fingers or wrist to inhibit the hand being inadvertently removed from grip element 105. Strap 125 may be used to moisten a hand of a user. Grip 105 may be made with electrically conductive material that allows for the flow of electricity in one or more directions. This material may include silver, copper, gold, aluminum, zinc, nickel, brass, iron, steel and any other electrically conductive material known to those skilled in the art. Strap 125 may be attached to base 120 and may attach to itself by means of hook and loop, snap fastener, button, buckle, knot etc. to wrap around the portion of the patient's body to be used as a ground. Gripping element 105 may be connected to base 120. Base 120 may allow grounding device 100 to be set on a flat surface to providing a non-slip surface between base 120 and a flat surface. Furthermore, because base 120 allow grounding device 100 to rest on a flat surface the patient can just rest his or her hand on grounding device 100 without having to hold it up. The less effort it takes maintain contact with the gripping element may increase contact, that in turn helps facilitate better bioelectric conductance readings. Better bioelectric conductance reading may increase the accuracy of diagnoses. Grounding device 100 may also include cord 115. Cord 115 may be a power cord that connect to an AC outlet. Grounding device 100 may also be powered by a battery. Alternately, cord 115 may be connected to one or more processors that control the bioelectrical grounding segments 110 to remove or combine one or more segments 110 to determine ground saturation. Moreover, processor may determine if moisture in one or more ground segment will increase ground saturation.

A computer algorithm and testing system of the disclosure runs a sequential testing of the plurality of incremental bioelectrical grounding segments 110 to determine the number of bioelectrical grounding segments 100 are required to establish ground saturation and to verify that the resistance reading remains the same or in an acceptable range from reading to reading. With all of the readings taken from point to point having the grounding area having an Ohm resistance reading within an equal or acceptable range, the readings are acceptably repeatable. This grounding technique becomes adaptable or dynamic. To reduce the complexity of having 20 bioelectrical grounding segments 110, a variety of different sized segments may be utilized by the disclosure. With the use of more segments and or a differing variety of segment sizes a more finite testing precision may be established than 5%. It is conceivable to establish a precision of 1% or even more finite as desired.

Figure 2A:
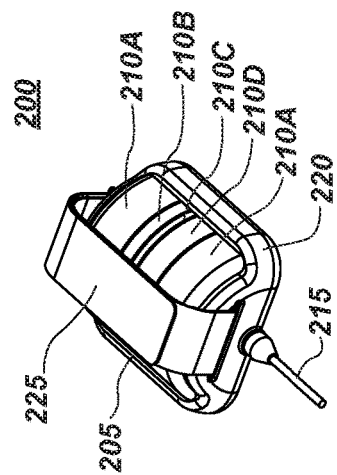
FIGS. 2A-2C illustrate a perspective view, top view and side view respectively of an arched grounding device with bioelectrical grounding segments of varyingly sized surface area.
Figure 2B:
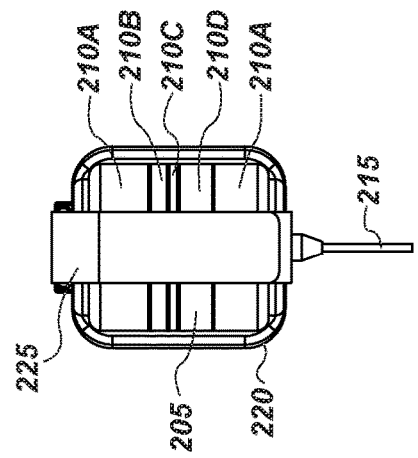
Figure 2C:
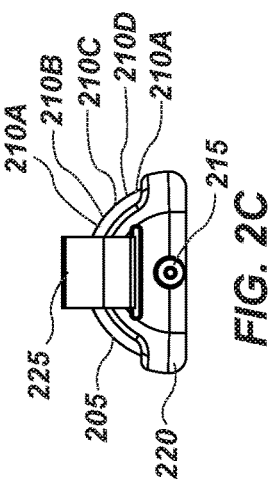

FIGS. 2A-2C illustrate a perspective view, top view, and side view respectively of an arched grounding device with bioelectrical grounding segments of varyingly sized surface area. Grounding device 200 is arched to allow the hand to rest comfortably to facilitate contact with grip element 205. Grip element 205 is the part of grounding device that contains grounding segment 210 and is to come in contact with a patient's body usually their hand and. Furthermore, the grounding elements may run perpendicular to a patient's fingers when place on grip element 205. Bioelectrical grounding segments 210 can be equal distances apart or they may be place at varying distances along the grip element. In this embodiment grip element has four different sized bioelectrical grounding segments.

Grounding segment 210A is about 35% of the top surface area of grip element 205 and may be placed at both ends of grip element. Grounding segment 210B is about 10% of the surface area of the grip element. Grounding segment 210C is the smallest segment with only 5% of the surface area that may contact the patient's body. The final grounding segment is 15% of the surface area of grip element 205 that is designed to come in contact with the patient's body.

Grip element 205 may have may different shapes and sizes to best meet the needs of the both the user and the patient. For example, grip element 205 may be arched to allow a patient to rest his or her arm on the table while the natural curvature of the hand rest over top of the arched grip element 205. Moreover, grip element 205 may be a flat, dome, cylindrical, double arched etc. and is attached to base 220. To aid in maintaining contact to grip element 205, strap 225 may be placed over the hand, fingers or wrist to inhibit the hand being inadvertently removed from grip element 205. Strap 225 may be attached to base 220 and may attach to itself by means of hook and loop, snap fastener, button, buckle, knot etc. around the portion of the patient's body that is used as a ground Gripping element 205 may be connected to base 220.

Base 220 may allow grounding device 200 to be set on a flat surface providing a non-slip surface between base 220 and a flat surface. Furthermore, because base 220 allow grounding device 200 to rest on a flat surface the patient can just rest his or her hand on grounding device 200 without having to hold it up. The less effort it takes maintain contact with the gripping element may increase contact, that in turn helps facilitate better bioelectric conductance readings. Better bioelectric conductance reading may increase the accuracy of diagnoses. Grounding device 200 may also include cord 215. Cord 215 may be a power cord that connect to an AC outlet. Grounding device 200 may also be powered by a battery. Alternately, cord 215 may be connected to one or more processors that control the bioelectrical grounding segments to activate or inactivate certain segments.

A computer algorithm and testing system of the disclosure runs a sequential testing of the plurality of incremental segments to determine the number of segments required to establish ground saturation and to verify that the resistance reading remains the same or in an acceptable range from reading to reading. With all of the readings taken from point to point having the grounding area having an Ohm resistance reading within an equal or acceptable range, the readings are acceptably repeatable. This grounding technique becomes adaptable or dynamic. To reduce the complexity of having 5 bioelectrical grounding segments 210, a variety of different sized segments may be utilized by the disclosure.

Figure 3A:
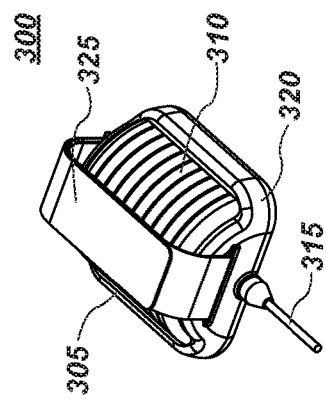
FIGS. 3A-3C illustrate a perspective view, top view, and side view respectively of an arched grounding device with bioelectrical grounding segments of intermediately sized surface area.
Figure 3B:
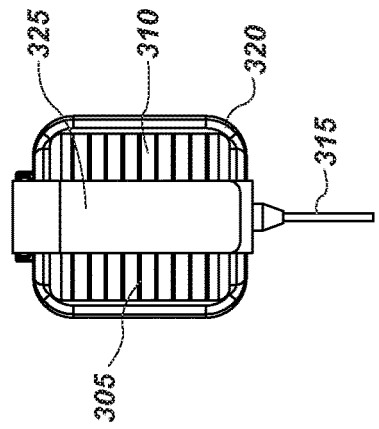
Figure 3C:
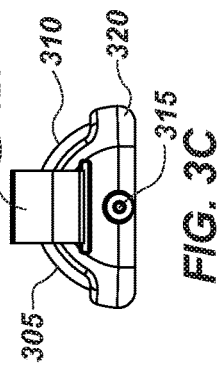

FIGS. 3A-3C illustrate a perspective view, top view, and side view respectively of an arched grounding device with bioelectrical grounding segments of intermediately sized surface area. Bioelectrical grounding segments 310 may be considered narrow when each segment consists of about 5% of the usable surface area on grip device 305. Narrowly sized bioelectrical grounding segments 310 may range from 1%-9.9% of the usable surface area on a grip device. Intermediately sized bioelectrical grounding segments 110 may range from 10%-19.9% of the usable surface area on a grip device. Lastly, widely sized bioelectrical grounding segments 110 would be 20% and greater of the usable surface area on a grip device. The usable surface excludes any side attached to base 320 and any other part not intended to come in contact with a patient's body.

Grounding device 300 is arched to allow the hand to rest comfortably to facilitate contact with grip element 305. Grip element 305 is the part of grounding device that contains grounding segment 310 and is to come in contact with a patient's body usually their hand. Bioelectrical grounding segments 310 can be equal distances apart or they may be place at varying distances along the grip element.

Grip element 305 may have may different shapes and sizes to best meet the needs of the both the user and the patient. For example, grip element 305 may be arched to allow a patient to rest his or her arm on the table while the natural curvature of the hand rest over top of the arched grip element 305. Moreover, grip element 305 may be a flat, hemispherical, cylindrical, double arched etc. and is attached to base 320. To aid in maintaining contact to grip element 305, strap 325 may be placed over the hand to inhibit the hand being inadvertently removed from grip element 305. Strap 325 may connect to base 320 and may attach to itself by means of hook and loop, snap fastener, button, buckle, knot etc. around the grounding portion of a patient's body. Gripping element 305 may be connected to base 320. Base 320 may allow grounding device 300 to be set on a flat surface providing a non-slip surface between base 320 and a flat surface. Furthermore, because base 320 allow grounding device 300 to rest on a flat surface the patient can just rest his or her hand on grounding device 300 without having to hold it up. The less effort it takes maintain contact with the gripping element may increase contact, that in turn helps facilitate better bioelectric conductance readings. Better bioelectric conductance reading may increase the accuracy of diagnoses. Grounding device 300 may also include cord 315. Cord 315 may be a power cord that connect to an AC outlet. Grounding device 300 may also be powered by a battery. Alternately, cord 315 may be connected to one or more processors that control the bioelectrical grounding segments to activate or inactivate certain segments.

A computer algorithm and testing system of the disclosure runs a sequential testing of the plurality of incremental segments to determine the number of segments required to establish ground saturation and to verify that the resistance reading remains the same or in an acceptable range from reading to reading. With all of the readings taken from point to point having the grounding area having an Ohm resistance reading within an equal or acceptable range, the readings are acceptably repeatable. This grounding technique becomes adaptable or dynamic. To reduce the complexity of having 10 bioelectrical grounding segments 310, a variety of different sized segments may be utilized by the disclosure.

Figure 4A:
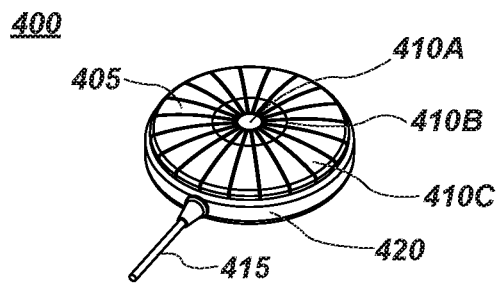
FIGS. 4A-4C illustrate a perspective view, top view, and side view respectively of a hemispherical grounding device with axial bioelectrical grounding segments.
Figure 4B:
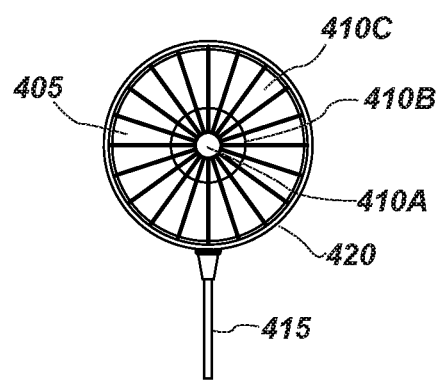
Figure 4C:
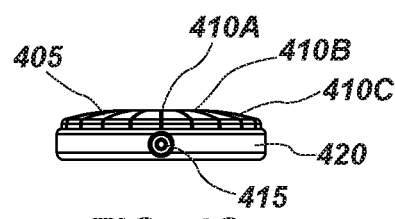

FIGS. 4A-4C illustrate a perspective view, top view, and side view respectively of a hemispherical grounding device with axial bioelectrical grounding segments. Bioelectrical grounding segments 410 may be considered narrow when each segment consists of about 5% of the usable surface area on grip device 405. Narrowly sized bioelectrical grounding segments 410 may range from 1%-9.9% of the usable surface area on a grip device. Intermediately sized bioelectrical grounding segments 410 may range from 10%-19.9% of the usable surface area on a grip device. Lastly, widely sized bioelectrical grounding segments 410 would be 20% and greater of the usable surface area on a grip device. The usable surface excludes any side attached to base 420 and any other part not intended to come in contact with a patient's body.

Grounding device 400 may include a hemispherical grip element 405 to allow the hand to rest comfortably to facilitate contact with grip element 405. Alternatively, grounding device 400 may include a flat grip element. Grip element 405 is the part of grounding device that contains grounding segment 410 and is to come in contact with a patient's body usually their hand. Bioelectrical grounding segments 410 can be equal distances apart or they may be place at varying distances along the grip element. Bioelectrical grounding segments 410 may be axial, extending from an axil point on grounding device 400. Grounding device 400 includes axial grounding segment that extend outward from an axis in the center of grip element 400. Furthermore, this embodiment includes three concentric segments. Grounding segment 410A is the innermost segment and may be absent of axial lines. Grounding segment 410B is the intermediate segment and may be further divided by axial lines. Lastly, grounding segment 410C is the outermost segment and this segment may be further divided by axial lines.

Grip element 405 may have may different shapes and sizes to best meet the needs of the both the user and the patient. For example, grip element 405 may be arched to allow a patient to rest his or her arm on the table while the natural curvature of the hand rest over top of the arched grip element 405. Moreover, grip element 405 may be a flat, dome, cylindrical, double arched etc. and is attached to base 420. To aid in maintaining contact to grip element 405, a strap, not shown, may be placed over the hand to inhibit the hand being inadvertently removed from grip element 405. The strap may connect to base 420 attaches to itself by means of hook and loop, snap fastener, button, buckle, knot etc. Gripping element may be connected to base 420. Base 420 may allow grounding device 400 to be set on a flat surface providing a non-slip surface between base 420 and a flat surface. Furthermore, because base 420 allow grounding device 400 to rest on a flat surface the patient can just rest his or her hand on grounding device 400 without having to hold it up. The less effort it takes maintain contact with the gripping element may increase contact, that in turn helps facilitate better bioelectric conductance readings. Better bioelectric conductance reading may increase the accuracy of diagnoses. Grounding device 400 may also include cord 415. Cord 415 may be a power cord that connect to an AC outlet. Grounding device 400 may also be powered by a battery. Alternately, cord 415 may be connected to one or more processors that control the bioelectrical grounding segments to activate or inactivate certain segments.

Figure 5A:
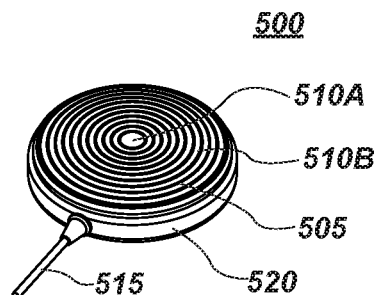
FIGS. 5A-5C illustrate a perspective view, top view, and side view respectively of a hemispherical grounding device with concentric bioelectrical grounding segments.
Figure 5B:
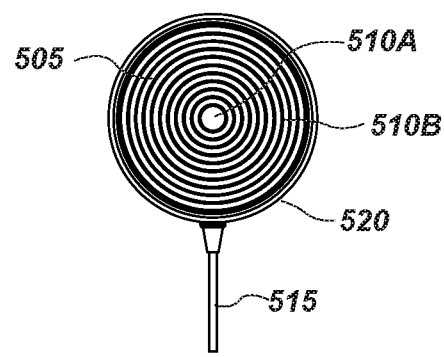
Figure 5C:
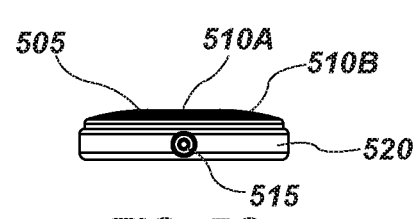

FIGS. 5A-5C illustrate a perspective view, top view, and side view respectively of a hemispherical grounding device with concentric bioelectrical grounding segments. Bioelectrical grounding segments 510 may be considered narrow when each segment consists of about 5% of the usable surface area on grip device 505. Moreover, concentric segments naturally increase in area as the outer diameters of ring-shaped segments increase. Even through each segment may generally have the same thickness from outer to inner diameters; one can see that the larger diameter rings have more area. This formation would naturally allow a variety of segment sizes.

Grounding device 500 may include a hemispherical grip element 505 to allow the hand to rest comfortably to facilitate contact with grip element 405. Alternatively, grounding device 500 may include a flat grip element. Grip element 505 is the part of grounding device that contains grounding segment 510 and is to come in contact with a patient's body usually their hand. Bioelectrical grounding segments 510 can be equal distances apart or they may be place at varying distances along the grip element. Bioelectrical grounding segments 510 may be axial, extending from an axil point on grounding device 500. Grounding device 500 includes concentric grounding segment 510A may be a small circle at the middle of grip element 505 then a larger and larger concentric bioelectrical grounding segments 510B extend outward from grounding segment 510A each subsequent concentric bioelectrical grounding segments 510B are depicted as equal distance apart. Another embodiment may include bioelectrical grounding segments 510B being at varying distances from each other.

Grip element 505 may have may different shapes and sizes to best meet the needs of the both the user and the patient. For example, grip element 505 may be arched to allow a patient to rest his or her arm on the table while the natural curvature of the hand rest over top of the arched grip element 505. Moreover, grip element 505 may be a flat, hemispherical, cylindrical, double arched etc. and is attached to base 520. To aid in maintaining contact to grip element 505, a strap, not shown, may be placed over the hand to inhibit the hand being inadvertently removed from grip element 505. The strap may connect to base 520 attaches to itself by means of hook and loop, snap fastener, button, buckle, knot etc. Gripping element may be connected to base 520. Base 520 may allow grounding device 500 to be set on a flat surface providing a non-slip surface between base 520 and a flat surface. Furthermore, because base 520 allow grounding device 500 to rest on a flat surface the patient can just rest his or her hand on grounding device 500 without having to hold it up. The less effort it takes maintain contact with the gripping element may increase contact, that in turn helps facilitate better bioelectric conductance readings. Better bioelectric conductance reading may increase the accuracy of diagnoses. Grounding device 500 may also include cord 515. Cord 515 may be a power cord that connect to an AC outlet. Grounding device 500 may also be powered by a battery. Alternately, cord 515 may be connected to one or more processors that control the bioelectrical grounding segments to activate or inactivate certain segments.

Figure 6A:
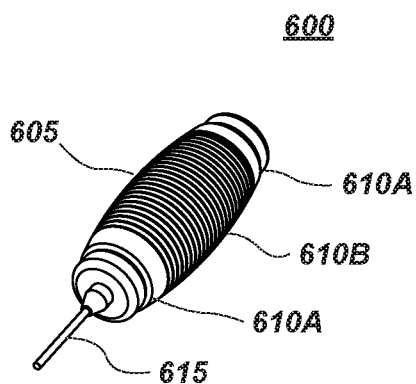
FIGS. 6A-6C illustrate a perspective view, top view, and side view respectively of a cylindrical grounding device with a plurality bioelectrical grounding segments of equal surface area.
Figure 6B:
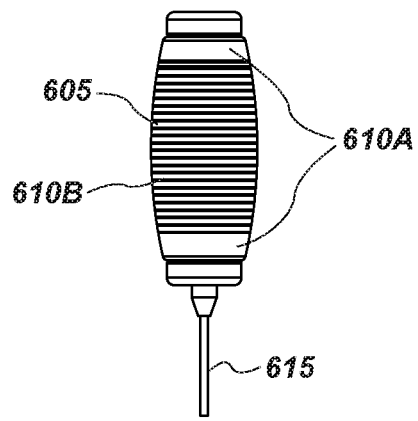
Figure 6C:
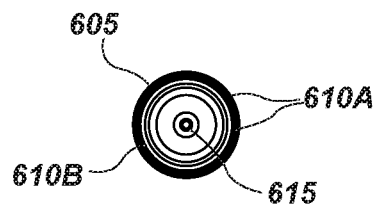

FIGS. 6A-6C illustrate a perspective view, top view, and side view respectively of a cylindrical grounding device with a plurality bioelectrical grounding segments of equal surface area. Bioelectrical grounding segments 610 may be considered narrow when each segment consists of about 5% of the usable surface area on grip device 605. Narrowly sized bioelectrical grounding segments 610 may range from 1%-9.9% of the usable surface area on a grip device. Intermediately sized bioelectrical grounding segments 610 may range from 10%-19.9% of the usable surface area on a grip device. Lastly, widely sized bioelectrical grounding segments 610 would be 20% and greater of the usable surface area on a grip device. The usable surface excludes any side attached to a base and any other part not intended to come in contact with a patient's body.

Grounding device 600 is cylindrical to allow the hand to grip comfortably to facilitate contact with grip element 605. Grip element 605 is the part of grounding device that contains grounding segment 610 and is to come in contact with a patient's body usually their hand. Bioelectrical grounding segments 610 can be equal distances apart, as depicted, or they may be place at varying distances along the grip element.

Grip element 605 may have may different shapes and sizes to best meet the needs of the both the user and the patient. Moreover, grip element 605 may be a flat, dome, cylindrical, double arched etc. and is attached to base 620. To aid in maintaining contact to grip element 605, strap, not shown, may be placed over the hand to inhibit the hand being inadvertently removed from grip element 605. A strap may be attached to one or more sides of base 620 and may attach to itself by means of hook and loop, snap fastener, button, buckle, knot etc. to wrap around the portion of the patient's body to be used as a ground. Gripping element 105 may be connected to a base. Grounding device 600 may also include cord 615. Cord 615 may be a power cord that connect to an AC outlet. Grounding device 600 may also be powered by a battery. Alternately, cord 615 may be connected to one or more processors that control the bioelectrical grounding segments to activate or inactivate certain segments.

A computer algorithm and testing system of the disclosure runs a sequential testing of the plurality of incremental bioelectrical grounding segments 610 to determine the number of segments required to establish ground saturation and to verify that the resistance reading remains the same or in an acceptable range from reading to reading. With all of the readings taken from point to point having the grounding area having an Ohm resistance reading within an equal or acceptable range, the readings are acceptably repeatable.

Figure 7A:
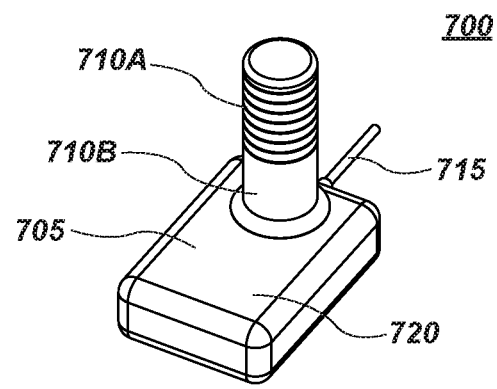
FIGS. 7A-7C illustrate a perspective view, top view, and side view respectively of a vertically based cylindrical grounding with bioelectrical grounding segments that are both large surface areas and narrow surface areas.
Figure 7B:
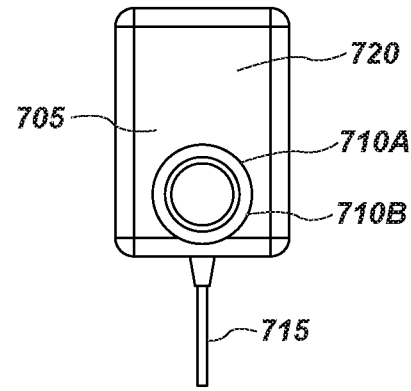
Figure 7C:
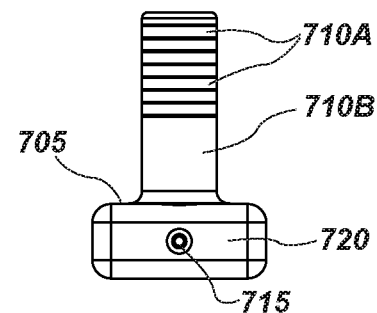

FIGS. 7A-7C illustrate a perspective view, top view, and side view respectively of a vertically based cylindrical grounding with bioelectrical grounding segments that are both large surface areas and narrow surface areas. Bioelectrical grounding segments 710 may be considered narrow when each segment consists of about 5% of the usable surface area on grip device 705. Narrowly sized bioelectrical grounding segments 710 may range from 1%-9.9% of the usable surface area on a grip device. Intermediately sized bioelectrical grounding segments 710 may range from 10%-19.9% of the usable surface area on a grip device. Lastly, widely sized bioelectrical grounding segments 110 would be 20% and greater of the usable surface area on a grip device. The usable surface excludes any side attached to base 720 and any other part not intended to come in contact with a patient's body.

Grounding device 700 is arched to allow the hand to rest comfortably to facilitate contact with grip element 705. Grip element 705 is the part of grounding device that contains grounding segment 710 and is to come in contact with a patient's body usually their hand. Bioelectrical grounding segments 710 can be equal distances apart or they may be place at varying distances along the grip element.

Grip element 705 may have may different shapes and sizes to best meet the needs of the both the user and the patient. For example, grip element 705 may be arched to allow a patient to rest his or her arm on the table while the natural curvature of the hand rest over top of the arched grip element 705. Moreover, grip element 705 may be a flat, dome, cylindrical, double arched etc. and is attached to base 720. To aid in maintaining contact to grip element 705, a strap may be placed over the hand to inhibit the hand being inadvertently removed from grip element 705. Gripping element 705 may be connected to base 720. Base 720 may allow grounding device 700 to be set on a flat surface providing a non-slip surface between base 720 and a flat surface. Furthermore, because base 720 allow grounding device 700 to rest on a flat surface the patient can just rest his or her hand on grounding device 700 without having to hold it up. The less effort it takes maintain contact with the gripping element may increase contact, that in turn helps facilitate better bioelectric conductance readings. Better bioelectric conductance reading may increase the accuracy of diagnoses. Grounding device 700 may also include cord 715. Cord 715 may be a power cord that connect to an AC outlet. Grounding device 700 may also be powered by a battery. Alternately, cord 715 may be connected to one or more processors that control the bioelectrical grounding segments to activate or inactivate certain segments.

A computer algorithm and testing system of the disclosure runs a sequential testing of the plurality of incremental bioelectrical grounding segments 710 to determine the number of segments required to establish ground saturation and to verify that the resistance reading remains the same or in an acceptable range from reading to reading. With all of the readings taken from point to point having the grounding area having an Ohm resistance reading within an equal or acceptable range, the readings are acceptably repeatable.

Figure 8:
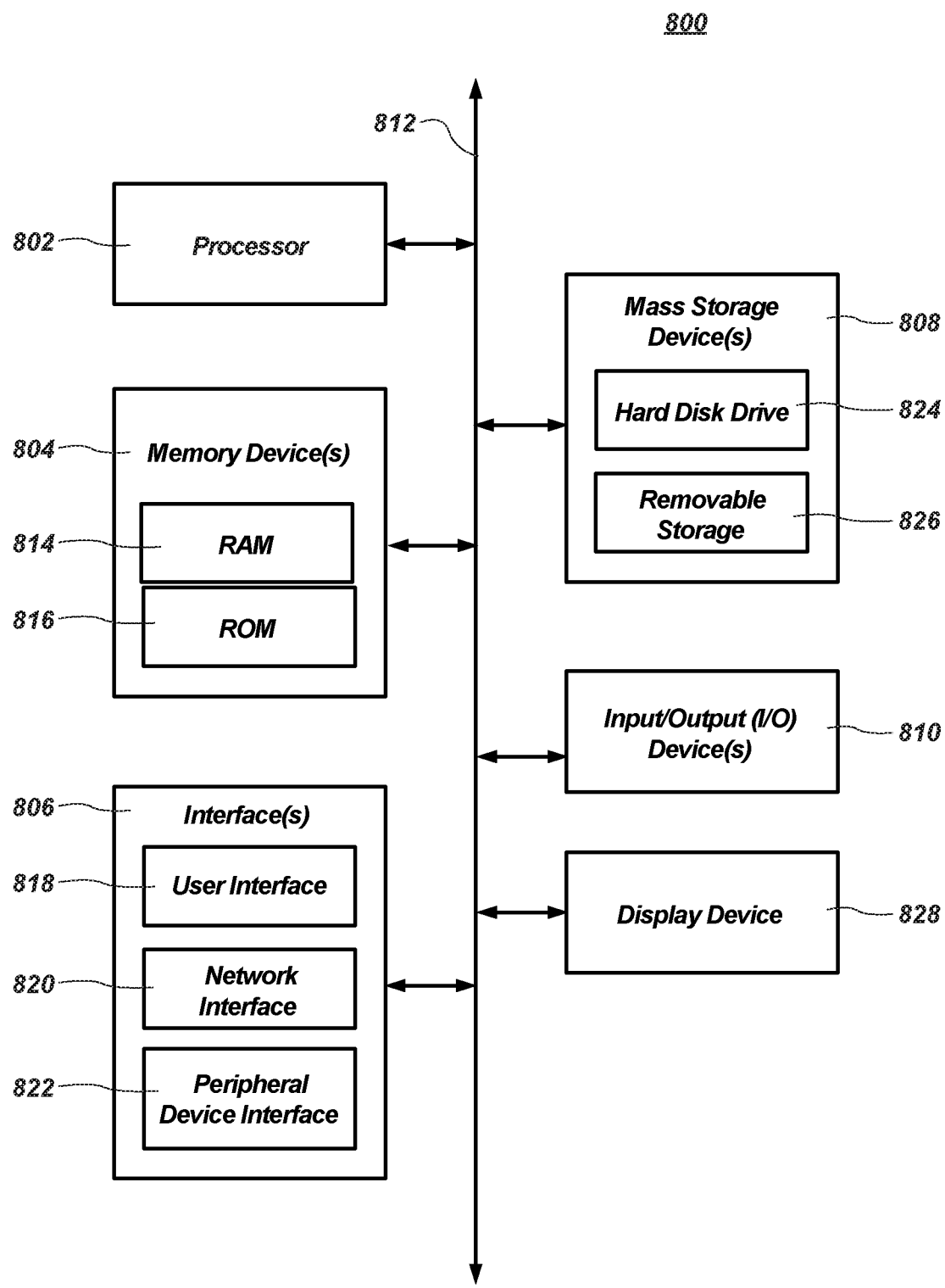
FIG. 8 illustrates a system of a computing device in accordance with the teachings and principles of the disclosure.

FIG. 8 illustrates a system of computing devices to collect and use bioelectrical information. Computing system 800 may be used to perform various procedures, such as those discussed herein. Computing system 800 can function as a server, a client, or any other computing entity. Computing system 800 can perform various monitoring functions as discussed herein, and can execute one or more application programs, such as the application programs described herein. Computing system 800 may include wide variety of computing devices, such as a desktop computer, a notebook computer, a server computer, a handheld computer, tablet computer and the like.

Computing system 800 includes one or more processors 802, one or more memory devices 804, one or more interfaces 806, one or more mass storage devices 808, one or more Input/Output (I/O) devices 810, and a display device 828 all of which are coupled to a bus 812. Processor(s) 802 include one or more processors or controllers that execute instructions stored in memory device(s) 804 and/or mass storage device(s) 808. Processor(s) 802 may also include various types of computer-readable media, such as cache memory.

Memory device(s) 804 include various computer-readable media, such as volatile memory (e.g., random access memory (RAM) 814) and/or nonvolatile memory (e.g., read-only memory (ROM) 816). Memory device(s) 804 may also include rewritable ROM 816, such as Flash memory.

Mass storage device(s) 808 include various computer readable media, such as magnetic tapes, magnetic disks, optical disks, solid-state memory (e.g., Flash memory), and so forth. As shown in FIG. 8, a particular mass storage device is a hard disk drive 824. Various drives may also be included in mass storage device(s) 808 to enable reading from and/or writing to the various computer readable media. Mass storage device(s) 808 include removable media 826 and/or non-removable media.

I/O device(s) 810 include various devices that allow data and/or other information to be input to or retrieved from computing device 800. Example I/O device(s) 810 include cursor control devices, keyboards, keypads, microphones, monitors or other display devices, speakers, printers, network interface cards, modems, lenses. CCDs or other image capture devices, and the like.

Display device 830 includes any type of device capable of displaying information to one or more users of computing system 800. Examples of display device 828 include a monitor, display terminal, video projection device, and the like.

Interface(s) 806 include various interfaces that allow computing system 800 to interact with other systems, devices, or computing environments. Example interface(s) 806 may include any number of different network interfaces 820, such as interfaces to local area networks (LANs), wide area networks (WANs), wireless networks, and the Internet. Other interface(s) include user interface 818 and peripheral device interface 822. The interface(s) 806 may also include one or more user interface elements 818. The interface(s) 806 may also include one or more peripheral interfaces such as interfaces for printers, pointing devices (mice, track pad, or any suitable user interface now known to those of ordinary skill in the field, or later discovered), keyboards, and the like.

Bus 812 allows processor(s) 802, memory device(s) 804, interface(s) 106, mass storage device(s) 808, and I/O device(s) 810 to communicate with one another, as well as other devices or components coupled to bus 812. Bus 812 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing system 800, and are executed by processor(s) 802. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Figure 9:
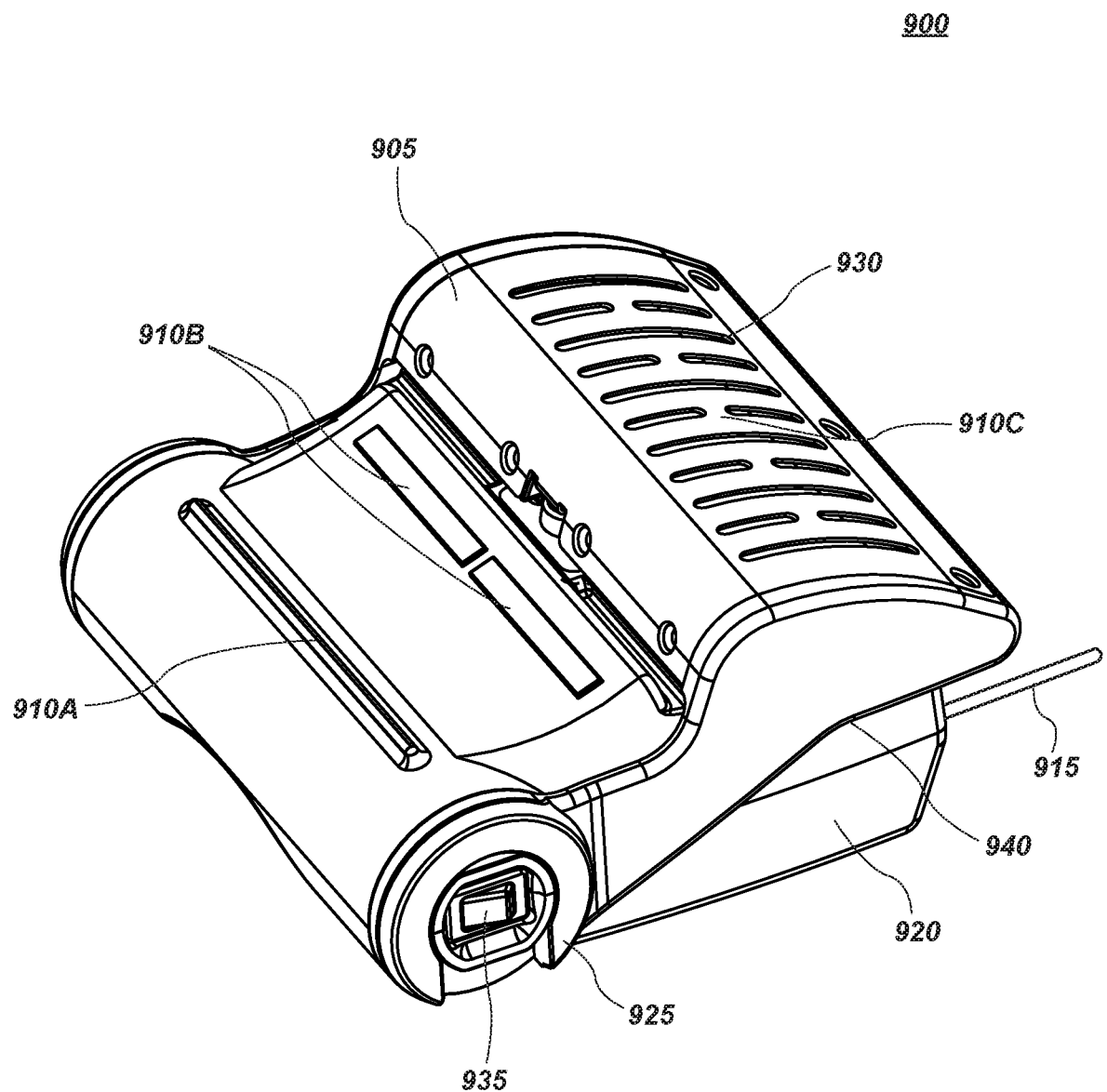
FIG. 9 illustrates perspective view of a hinged grounding device with a moisture pad.

FIG. 9 illustrates perspective view of a hinged grounding device with a moisture pad. Bioelectrical grounding segments 910 may be found in three different locations. Bioelectrical grounding segments 910A are found near the proximal end of grounding device 900 and may be located above hinge 925. Bioelectrical grounding segments 910A may include a single segment, as depicted, or may have multiple segments. Bioelectrical grounding segments 910B are found in between bioelectrical grounding segments 910A and 910C. Bioelectrical grounding segments rounding segments 910C may include one or more segments. Lastly, bioelectrical grounding segments 910C may be found on the distal end of grounding device 900. Bioelectrical grounding segments 910C may include moisture apertures 930. Moisture apertures 930 may be various shapes and sizes and may include a design or logo. Moisture pad 940 may be located beneath moisture aperture 930 and on top of base 920. Moisture pad 930 may be comprised at least partially as absorbent material for example a sponge. Moister pad 930 may also be material similar to a washcloth or a paper towel etc.

In use, a wrist or heal of the hand may be placed on top of bioelectrical grounding segments 910A. Then the heel to the palm of the hand may contact bioelectrical grounding segments 910B and then the palm or the fingers may contact bioelectrical grounding segments 910C. As the hand rest on grounding device 900, the proximal portion of grip element 905 pivots at hinge 940 and the distal end of grip element 905 is pressed downward causing moisture from moisture pad 940 to expels water or other electrically conductive liquid out of moisture pad 940 and through moisture apertures 930 moistening the hand and increasing grounding capacity. Alternatively, a hand may be place on the grip member 905 by placing the palm of the hand over grounding segment 910C with fingers contacting bioelectrical grounding segments 910B and 910A.

Grounding device 900 may have may different shapes and sizes to best meet the needs of the both the user and the patient. For example, grip element 905 may be or arched or double arched to allow a patient to rest his or her arm on the table while the natural curvature of the hand rest over top of the arched grip element 905. Moreover, grip element 905 may be a flat, dome, cylindrical, double arched etc. and is attached to base 920. Maintain Contact. To aid in maintaining contact to grip element 905, a strap may be placed over the hand to inhibit the hand being inadvertently removed from grip element 905.

Large grounding segment 910C that is big enough to provide ample ground for patients with moist hands in a bio-conductance test is used in conjunction with 2 smaller bioelectrical grounding segments 910A and 910B. A circuit could be formed with one small segment and the large grounding segment 910C and a moistened hand. A conductance reading could be taken and then another segment could be added to see if there is a conductivity change to first reading. If there is no increase to the conductivity reading then it can be determined that saturation is met. If there is an increase to the conductivity reading then it can be determined that saturation is not met and an alert provided to instruct to have more moisture added the test subject hand contacting the bioelectrical grounding segments 910 C above moisture pad 940. Also, a frequent continuity test could be performed between 2 segments in contact with the hand to make sure that the hand remains constantly in contact with the bioelectrical grounding segments 910. In the event that the continuity test indicated a broken continuity circuit, then the system can alert the technician the test subject has removed a hand from the test circuit and compromised the reading. The reading could be invalidated and retaken.

Gripping element 905 may be connected to base 920 by hinge 925. Base 920 may allow grounding device 900 to be set on a flat surface providing a non-slip surface between base 920 and a flat surface. Furthermore, because base 920 allow grounding device 900 to rest on a flat surface the patient can just rest his or her hand on grounding device 900 without having to hold it up. The less effort it takes maintain contact with the gripping element may increase contact, that in turn helps facilitate better bioelectric conductance readings. Better bioelectric conductance reading may increase the accuracy of diagnoses.

In the unlikely event that through moistening the grounding hand, the new ground saturation resistance becomes lower than the previous ground saturation resistance, the system could systematically remove segments 910A, 910B and or 910C from the circuit to create a new configuration of segments 910A. 910B and or 910C that would have a grounding area that would have an consistent ground resistance in an acceptable range of the previous ground saturation resistance.

Grounding device 900 may also include switch 935 and cord 915. Cord 915 may be a power cord that connect to an AC outlet and switch 935 may turn off and on Grounding device. Grounding device 900 may also be powered by a battery in which switch 935 can turn it off and on. Alternately, cord 915 may be connected to one or more processors that control bioelectrical grounding segments 910 to activate or inactivate certain segments.

A computer algorithm and testing system of the disclosure runs a sequential testing of the plurality of incremental bioelectrical grounding segments 910 to determine the number of segments required to establish ground saturation and to verify that the resistance reading remains the same or in an acceptable range from reading to reading. With all of the readings taken from point to point having the grounding area having an Ohm resistance reading within an equal or acceptable range, the readings are acceptably repeatable.

However, there are potential problems in the situation where the size of the subject's hand squeezing the device is not large enough to cover all of the plurality of segments. Also, in the manufacturing process it may be preferred to have most of the plurality of segments be the same size or area, i.e., the same part, to take advantage of scales of economy and reduce part numbers and inventory. With this in mind, a possible configuration of the plurality of brass segments may be to have one larger segment that would be covered by about 50% of a smaller squeezing hand from possibly a smaller test subject, such as a female or a child. The rest of the brass segments making up the reference area of the device could be comprised of smaller segments of the same size.

In an embodiment, the device may incorporate a registration locator into the larger brass segment so that all hand sizes that grab the reference portion of the device naturally place the base of their palm against this registration locator with the rest of their palm enveloping the rest of the large segment and at least one of the smaller segments. The system would then be able to determine how many of the segments are contacting the gripping hand and place them into the active grounding side of the testing circuit. The ground saturation algorithm would then dynamically adapt to only evaluate those segments that are active in the circuit. Thus, the subject's hand remains in contact with enough grounding area to maintain ground saturation or the conductance of the grounding area could drop out of an acceptable range leaving this test to be unacceptable and repeated with a test that has an acceptable ground resistance.

The total grounding area may be at least 5 square inches to establish some margin of extra ground area to maintain ground saturation and a constant ground resistance reading even if the moisture on the hands evaporates causing the contacting area to enlarge to maintain ground saturation. In an embodiment, the total grounding area of the device may be at least 9 square inches to increase the acceptable margins.

In the event that the hands become so dry that the entire contacting area has a resistance higher than the establish ground saturation resistance, the system will alert the technician to stop the test to moisten the grounding hand to bring the ground resistance reading back to the accepted range of the earlier tests.

EXAMPLES

Example 1 is a device comprising one or more of the following components, namely: a multi segmented grounding module comprising a plurality of segments.

In Example 2, the grounding module of Example 1 is ergonomically shaped to fit the palm of hand.

In Example 3, the device as in any of Examples 1-2, wherein the device may further comprise one or more connectors that can move from left to right sides of the device to accommodate switching from left hand to right hand.

In Example 4, the device as in any of Examples 1-3, the device may further comprise a grounding surface that is made from brass or any conductive material.

In Example 5, the device as in any of Examples 1-4, the grounding surface creates a cylindrical shape, a semi cylindrical shape, a pancake or mushroom shape or any shape that would conform to an appropriate part of the body for grounding.

In Example 6, the device as in any of Examples 1-5, wherein the plurality of segments are equal sized and in any number of segments.

In Example 7, the device as in any of Examples 1-6, wherein the plurality of segments may be shaped to aid in positioning the hand.

In Example 8, the device as in any of Examples 1-7, wherein the plurality of segments vary in size or a combination of equal and varied sizes.

In Example 9, the device as in any of Examples 1-8, wherein the plurality of segments are isolated from each other and can be used exclusively or in any combination of other segments.

In Example 10, the device as in any of Examples 1-9, wherein the plurality of segments are combined with other segments to become the total grounding area.

In Example 11, the device as in any of Examples 1-10, the device further comprising a small conductive contact that is used in conjunction with segments in the ground resistance measurement.

In Example 12, the device as in any of Examples 1-11, wherein one of the plurality of segments is used with other segments in the ground resistance measurement.

In Example 13, the device as in any of Examples 1-12, wherein the plurality of segments are arranged to create the grounding area in a linear fashion, axially, concentrically or any configuration.

In Example 14, the device as in any of Examples 1-13, wherein the grounding area is any size that will adequately achieve ground saturation with any person's hands no matter how dry with extra area to have a margin of error.

In Example 15, the device as in any of Examples 1-14, wherein the device is part of a system that sequentially and incrementally tests all possible configurations of segments throughout the entire device to establish the percentage of segments required to obtain ground saturation or a ground saturation resistance.

In Example 16, the device as in any of Examples 1-15, wherein the system has the ability to determine if some of the segments are out of the range of the patient's hands and not part of the grounding circuit, wherein the system determines all of the segments that are part of the grounding circuit, and wherein the system uses only those active segments to determine a ground saturation resistance.

In Example 17, the device as in any of Examples 1-16, wherein the system monitors the number of segments required to maintain a constant ground saturation resistance, and wherein the system notifies the technician of the percentage of segments required to maintain the saturation resistance, and wherein the system recommends moistening the grounding hand at a predetermined percentage threshold, which threshold is adjustable in the system.

In Example 18, the device as in any of Examples 1-17, wherein the system requires a new point test if the test was performed with a grounding resistance out of an acceptable range.

In Example 19, the device as in any of Examples 1-18, wherein the system reduces the percentage of segments used in testing circuit to maintain a grounding resistance established in earlier point readings.

In Example 20, the device as in any of Examples 1-19, wherein the device further comprises a strap that is incorporated to ensure the hand to grounding area contact is secure and unchanging or in situations where the individual cannot maintain a secure grip.

In Example 21, the device as in any of Example 1-20, wherein the system utilizes 2 segments in contact with test subject to perform a continuity test to establish if the test subjects hand continues to be in contact with the bioelectrical grounding segments.

Example 22 is a grounding device comprising namely a grip element; and one or more bioelectrical grounding segments. In an example, the one or more bioelectrical grounding segments may be disposed about the grip element on the grounding device.

In Example 23, the grounding device of Example 22, further comprising a cord connected to the grounding device.

In Example 24, the grounding device of Examples 22-23, further comprising a base connected to the grip element.

In Example 25, the grounding device of Examples 22-24, further comprising a strap connected to the grounding device.

In Example 26, the grounding device of Examples 22-25, wherein the bioelectrical grounding segments are arched.

In Example 27, The grounding device of Example 22-26, wherein the one or more bioelectrical grounding segments have an equal surface area.

In Example 28, the grounding device of Example 22-27, wherein the one or more bioelectrical grounding segments have varying surface areas with respect to each of the other one or more bioelectrical grounding segments.

In Example 29 the grounding device of Example 22-28, wherein the one or more bioelectrical ground segments are comprised of electrically conductive material.

In Example 30, the grounding device of Example 22-29, wherein the grounding device is cylindrical.

In Example 31, the grounding device of Example 22-30, further comprising a base.

In Example 32, the grounding device of Example 22-31, wherein a top of the grounding device is hemispherical.

In Example 33, the grounding device of Example 22-32, further comprising a hinge.

In Example 34, the grounding device of Example 22-33, further comprising a moisture pad.

In Example 35, the grounding device of claim 13, further comprising one or more moisture aperture.

Example 36 is a system comprising namely a processor that detects a grounding reading from one or more bioelectrical grounding segments, determines which of the one or more bioelectrical grounding segments provide ground saturation; and a grounding device comprising namely a grip element, and one or more bioelectrical grounding segments.

In Example 37, the system of Example 36-, wherein a processor determines whether or not a moisture content of one or more grounding segments provides ground saturation.

In Example 38 the system of Example 36-37, wherein a processor determines if one or more bioelectrical grounding segments should be excluded from the ground saturation determination.

In Example 39 the system of Example 36-38, wherein one or more bioelectrical grounding segments includes a surface area that is different from another one of the one or more bioelectrical grounding segments.

In Example 40 the system of Example 36-39, wherein the grounding device grounds a person in response to contacting a person.

Example 41 the system of Example 36-40, wherein the processor determines whether or not one or more bioelectrical ground segments is in contact with a person.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A grounding device comprising:
an arched grip element extending along an axis; and
a plurality of narrowly-sized bioelectrical grounding segments disposed about the arched grip element in a direction transverse to the axis, wherein the arched grip element increases contact between the plurality of narrowly-sized bioelectrical grounding segments and a person.

2. The grounding device of claim 1, further comprising a cord connected to the grounding device.

3. The grounding device of claim 1, further comprising a base connected to the grip element.

4. The grounding device of claim 1, further comprising a strap connected to the grounding device.

5. The grounding device of claim 1, wherein the plurality of narrowly-sized bioelectrical grounding segments are equally spaced about the arched grip element.

6. The grounding device of claim 1, wherein the each of the plurality of narrowly-sized bioelectrical grounding segments has a varying surface area with respect to each other of the plurality of narrowly-sized bioelectrical grounding segments.

7. The grounding device of claim 1, wherein each of the plurality of narrowly-sized bioelectrical ground segments is comprised of electrically conductive material.

8. The grounding device of claim 1, wherein the grounding device is cylindrical.

9. The grounding device of claim 1, further comprising a base.

10. The grounding device of claim 1, wherein a top of the grounding device is hemispherical.

11. The grounding device of claim 1, further comprising a hinge.

12. The grounding device of claim 11, further comprising a moisture pad.

13. The grounding device of claim 12, further comprising one or more moisture apertures.

14. The grounding device of claim 1, wherein each of the plurality of narrowly-sized bioelectrical grounding segments has an equal surface area.

15. A system comprising:
a processor that detects a grounding reading from one or more bioelectrical grounding segments and determines which of the one or more bioelectrical grounding segments provides ground saturation; and
a grounding device comprising:
an arched grip element extending along an axis; and
a plurality of narrowly-sized bioelectrical grounding segments disposed about the arched grip element in a direction transverse to the axis, wherein the arched grip element increases contact between the plurality of narrowly-sized bioelectrical grounding segments and a person.

16. The system of claim 15, wherein the processor determines whether or not a moisture content of the plurality of narrowly-sized grounding segments provides ground saturation.

17. The system of claim 15, wherein the processor determines if the plurality of narrowly-sized bioelectrical grounding segments should be excluded from the ground saturation determination.

18. The system of claim 15, wherein each of the plurality of narrowly-sized bioelectrical grounding segments includes a surface area that is different from another one of the plurality of narrowly-sized bioelectrical grounding segments.

19. The system of claim 15, wherein the grounding device grounds a person in response to contacting the person.

20. The system of claim 19, wherein the processor determines whether or not each of the plurality of narrowly-sized bioelectrical ground segments is in contact with the person.

* * * * *